US011351552B2

(12) United States Patent
Fukuzawa et al.

(10) Patent No.: US 11,351,552 B2
(45) Date of Patent: Jun. 7, 2022

(54) REACTION PROCESSOR, REACTION PROCESSING VESSEL, AND REACTION PROCESSING METHOD

(71) Applicants: Nippon Sheet Glass Company, Limited, Tokyo (JP); National Institute of Advanced Industrial Science and Technology, Tokyo (JP)

(72) Inventors: Takashi Fukuzawa, Tokyo (JP); Hidenori Nagai, Osaka (JP)

(73) Assignees: Nippon Sheet Glass Company, Limited, Tokyo (JP); National Institute of Advanced Industrial Science and Technology, Tokyo (JP)

( * ) Notice: Subject to any disclaimer, the term of this patent is extended or adjusted under 35 U.S.C. 154(b) by 276 days.

(21) Appl. No.: 16/025,398

(22) Filed: Jul. 2, 2018

(65) Prior Publication Data

US 2018/0311673 A1    Nov. 1, 2018

Related U.S. Application Data

(63) Continuation of application No. PCT/JP2016/089041, filed on Dec. 28, 2016.

(30) Foreign Application Priority Data

Jan. 5, 2016    (JP) .............................. JP2016-000693

(51) Int. Cl.
*B01L 7/00*    (2006.01)
*B01L 3/02*    (2006.01)
(Continued)

(52) U.S. Cl.
CPC ............... *B01L 7/52* (2013.01); *B01L 3/0289* (2013.01); *B01L 3/50273* (2013.01);
(Continued)

(58) Field of Classification Search
CPC ....... B01L 2200/026; B01L 2200/0684; B01L 2200/0694; B01L 2200/10;
(Continued)

(56) References Cited

U.S. PATENT DOCUMENTS 5,587,128 A    12/1996  Wilding et al.
5,726,404 A    3/1998   Brody
(Continued)

FOREIGN PATENT DOCUMENTS

CN    1816393 A      8/2006
EP    1 614 466 A2   1/2006
(Continued)

OTHER PUBLICATIONS

Communication dated Mar. 14, 2019, from the Intellectual Property Office of Singapore in counterpart application No. 11201805707V.
(Continued)

*Primary Examiner* — Lydia Edwards
(74) *Attorney, Agent, or Firm* — Sughrue Mion, PLLC

(57) ABSTRACT

A reaction processor includes: a reaction processing vessel placing portion for placing a reaction processing vessel provided with a channel into which a sample is introduced; a temperature control system, which controls the temperature of the channel in order to heat the sample inside the channel; and a liquid feeding system, which controls the pressure inside the channel of the reaction processing vessel in order to move the sample inside the channel. The liquid feeding system maintains the pressure inside the channel to be higher than the atmospheric pressure in the surrounding of the reaction processing vessel, more preferably 1 atm or higher, during a reaction process of the sample.

11 Claims, 6 Drawing Sheets

(51) Int. Cl.
    *B01L 3/00* (2006.01)
    *C12Q 1/6806* (2018.01)
    *C12Q 1/686* (2018.01)
    *G01N 21/78* (2006.01)
    *C12N 15/09* (2006.01)
    *C12M 1/00* (2006.01)
    *C12Q 1/68* (2018.01)

(52) U.S. Cl.
    CPC ......... *B01L 3/502746* (2013.01); *B01L 7/525* (2013.01); *C12M 1/00* (2013.01); *C12N 15/09* (2013.01); *C12Q 1/6806* (2013.01); *G01N 21/78* (2013.01); B01L 3/502715 (2013.01); B01L 2200/026 (2013.01); B01L 2200/0684 (2013.01); B01L 2200/0694 (2013.01); B01L 2200/10 (2013.01); B01L 2300/0816 (2013.01); B01L 2300/0883 (2013.01); B01L 2300/14 (2013.01); B01L 2400/0481 (2013.01); B01L 2400/0487 (2013.01); C12Q 1/68 (2013.01); C12Q 1/686 (2013.01)

(58) Field of Classification Search
    CPC ..... B01L 2300/0816; B01L 2300/0883; B01L 2300/14; B01L 2400/0481; B01L 2400/0487; B01L 3/0289; B01L 3/502715; B01L 3/50273; B01L 3/502746; B01L 7/52; B01L 7/525; C12M 1/00; C12N 15/09; G01N 21/78; C12Q 1/686; C12Q 1/68; C12Q 1/6806
    See application file for complete search history.

(56) References Cited

U.S. PATENT DOCUMENTS

| | | | |
|---|---|---|---|
| 2002/0075363 A1 | 6/2002 | McNeely et al. | |
| 2003/0008308 A1* | 1/2003 | Enzelberger | B01F 13/0059 435/6.19 |
| 2006/0275179 A1 | 12/2006 | Viovy et al. | |
| 2007/0248958 A1* | 10/2007 | Jovanovich | B01L 3/50273 435/6.19 |
| 2008/0241844 A1 | 10/2008 | Kellogg | |
| 2009/0320930 A1 | 12/2009 | Zeng et al. | |
| 2010/0200402 A1 | 8/2010 | Li et al. | |
| 2012/0178091 A1* | 7/2012 | Glezer | B01L 3/5027 435/6.12 |

FOREIGN PATENT DOCUMENTS

| | | |
|---|---|---|
| JP | 9-262084 A | 10/1997 |
| JP | 2001173598 A | 6/2001 |
| JP | 2001238663 A | 9/2001 |
| JP | 2007-300896 A | 11/2007 |
| JP | 2009-517075 A | 4/2009 |
| JP | 2009525728 A | 7/2009 |
| JP | 2009-232700 A | 10/2009 |
| JP | 2010-528264 A | 8/2010 |
| JP | 2011-30522 A | 2/2011 |
| JP | 2013-55921 A | 3/2013 |
| JP | 2015-139379 A | 8/2015 |
| WO | 2013/132645 A1 | 9/2013 |

OTHER PUBLICATIONS

Communication dated Nov. 5, 2019 from the Japanese Patent Office in application No. 2017-560368.
Communication dated Nov. 27, 2019 from the European Patent Office in application No. 16883881.1.
Communication dated Jul. 24, 2019, from the European Patent Office in counterpart European Application No. 16883881.1.
International Search Report dated Apr. 11, 2017 from the International Bureau in counterpart International Application No. PCT/JP2016/089041.
International Preliminary Report on Patentability dated Jul. 19, 2018 from the International Bureau in counterpart International Application No. PCT/JP2016/089041.
Klemm et al., "Magnetic particle-based sample-prep and valveing in microfluidic devices," Microfluidics, BioMEMS, and Medical Microsystems X; vol. 8251 (2012) 7 pages total.
Communication dated Nov. 2, 2020 from the Indian Intellectual Property Patent Office in Application No. 201817028594, English Translation.
Office Action dated Mar. 9, 2021 issued by the Chinese Patent Office in Chinese Application No. 201680076075.5, English Translation.
Office Action dated Jan. 11, 2022 from the Japanese Patent Office in JP Application No. 2020-181773.

* cited by examiner

REACTION PROCESSOR, REACTION PROCESSING VESSEL, AND REACTION PROCESSING METHOD

BACKGROUND OF THE INVENTION

1. Field of the Invention

The present invention relates to reaction processors, reaction processing vessels, and reaction processing methods used for polymerase chain reactions (PCR).

BACKGROUND ART

Genetic testing is widely used for examinations in a wide variety of medical fields, identification of farm products and pathogenic microorganisms, safety assessment for food products, and even for examinations for pathogenic viruses and a variety of infectious diseases. In order to detect with high sensitivity a minute amount of gene's DNA, methods of analyzing the resultant obtained by amplifying a portion of DNA are known. Above all, PCR is a remarkable technology where a certain portion of a very small amount of DNA collected from an organism or the like is selectively amplified.

In PCR, a predetermined thermal cycle is applied to a sample in which a biological sample containing DNA and a PCR reagent consisting of primers, enzymes, and the like are mixed so as to cause reactions such as denaturation, annealing, and elongation to be repeated so that a specific portion of DNA is selectively amplified.

It is a common practice to perform the processing of a reaction where a minute amount of sample is used such as PCR in a container called a vial or in a channel formed on a chip. For miniaturization and speeding up, technologies for performing PCR in a channel are sometimes advantageous, and many aspects thereof have been put to practical use.

In a thermal cycle of PCR, it is necessary to repeat a temperature cycle from a low temperature of at least about 50° C. to a high temperature of about 95° C. for a predetermined number of times for a sample in which DNA to be amplified and a PCR reagent are mixed. Since the sample is normally an aqueous solution, the vapor pressure becomes high in the 95° C. range, and the water content of the sample is likely to evaporate. If the water content of the sample evaporates, the concentration of the sample may become high, and parameters such as the optical characteristics of the sample may unexpectedly change, possibly causing problems such as not being able to properly manage the reaction processing step. Particularly in real-time PCR etc., since it is necessary to continually monitor the optical properties, etc., of the sample while performing PCR, there is a possibility that the progress of the reaction processing cannot be kept track of. Also, if bubbles are generated in the channel due to the evaporation of the sample, there is a possibility that the movement of the sample existing in the channel is prevented by the bubbles.

Particularly, when the place where PCR is performed is in an environment with low atmospheric pressure such as a high altitude place, this becomes a particularly apparent problem. In other words, since the atmospheric pressure decreases as the altitude increases, the boiling point drops remarkably in such an environment, causing the sample to boil easily. For example, the atmospheric pressure is roughly 897 hPa and the boiling point is 96.6° C. according to calculations at a place where the altitude is 1000 m, the atmospheric pressure is 845 hPa and the boiling point is 95° C. at a place where the altitude is 1500 m, and the atmospheric pressure is 797 hPa and the boiling point is 93.4° C. at a place where the altitude is 2000 m. Such high altitude places include Denver (altitude of about 1600 m), Mexico City (altitude of about 2200 m), etc. In such places, the sample boils easily in a high temperature range and thus vaporizes and/or foams, or the evaporation of the sample becomes remarkable; thus, it is difficult to practically perform PCR.

Also, the pressure inside a passenger airplane is about 800 hPa, which is equal to about 2000 m in altitude, and the boiling point is about 93° C., meaning that it is practically difficult to perform PCR even inside an airplane in flight. This means that a circumstance occurs that becomes an obstacle for taking immediate preventive measures for recognizing the existence of viruses, pathogens, etc., in an airplane so as to prevent them before entering the country in order to prevent their worldwide spread. Also in flatlands, by raising the temperature of a sample mainly composed of an aqueous solution to around 95° C., the sample is very likely to evaporate partially although the sample does not come to a boil, and a fluorescence signal may not be measured accurately in the case of performing PCR inside a channel.

In view of this, for the purpose of preventing a decrease in volume due to evaporation of a sample or the like, a configuration has been suggested in the related art where a liquid having a low vapor pressure (a high boiling point) such as oil is arranged at both ends of the sample so as to allow the liquid to function as a so-called "lid" (see, for example, Patent Document 1). By putting a "lid" using a non-volatile liquid on both sides of the sample, the evaporation of the sample can be prevented.

Further, a structure has been proposed where air bubbles generated inside a channel are positively discharged from the channel by providing a gas hole, a hydrophobic filter, or the like in the channel (see, for example, Patent Document 2).

[Patent Document 1] Japanese Patent Application Publication No. 2009-232700
[Patent Document 2] Japanese Patent Application Publication No. H9-262084

SUMMARY OF THE INVENTION

However, as described in Patent Document 1, it is very troublesome to prepare for a task of putting a lid using oil or the like in such a manner that a sample subjected to PCR is sandwiched, and there is also a problem in terms of preventing contamination of the sample. Furthermore, in an embodiment according to Patent Document 1, it is considered that there is a case where boiling of a sample cannot be prevented under an environment where the boiling point of the sample becomes low.

Also, as described in Patent Document 2, positively removing air bubbles from a channel is not a fundamental solution from the viewpoint of preventing a decrease in volume caused due to the boiling and/or evaporation of a sample, and, more than anything, the concentration of the sample may rise.

In this background, a purpose of the present invention is to provide a reaction processor, a reaction processing vessel, and a reaction processing method capable of performing PCR while preventing the boiling of a sample and the generation of air bubbles even in a place where the air pressure is low.

A reaction processor according to one embodiment of the present invention includes: a placing portion for placing a plate-like reaction processing vessel that is provided with a channel into which a sample is introduced; a temperature control system that controls the temperature of a region in which the channel exists in order to heat the sample inside the channel; and a liquid feeding system that controls the pressure inside the channel of the reaction processing vessel so as to move the sample inside the channel. Further, the liquid feeding system maintains the pressure inside the channel during a reaction process of the sample to be higher than the air pressure in the surrounding environment of the reaction processor, preferably 1 atm or higher.

The liquid feeding system may include a pressurizing chamber that has an internal pressure maintained to be higher than the air pressure in the surrounding environment of the reaction processor, preferably 1 atm or higher; and a liquid feeding pump that is arranged inside the pressurizing chamber. The output of the liquid feeding pump may communicate with a first communication port that is provided at one end of the channel of the reaction processing vessel, and the inside of the pressurizing chamber may communicate with a second communication port that is provided at the other end of the channel of the reaction processing vessel. The reaction processor may further include a control unit that controls the liquid feeding pump in order to move the sample inside the channel.

The liquid feeding system may include a pressurizing chamber that has an internal pressure maintained to be higher than the air pressure in the surrounding environment of the reaction processor, preferably 1 atm or higher; a first liquid feeding pump that is arranged inside the pressurizing chamber; and a second liquid feeding pump that is arranged inside the pressurizing chamber. The output of the first liquid feeding pump may communicate with a first communication port that is provided at one end of the channel of the reaction processing vessel, and the output of the second liquid feeding pump may communicate with a second communication port that is provided at the other end of the channel of the reaction processing vessel. The reaction processor may further include a control unit that controls the first liquid feeding pump and the second liquid feeding pump in order to move the sample inside the channel.

The liquid feeding system may include: a pressurizing chamber that has an internal pressure maintained to be higher than the air pressure in the surrounding environment of the reaction processor, preferably 1 atm or higher; a liquid feeding chamber that has an internal pressure maintained to be a pressure that is higher than that inside the pressurizing chamber; a first direction switching valve that allows either one of the pressurizing chamber and the liquid feeding chamber to communicate with a first communication port provided at one end of the channel of the reaction processing vessel; and a second direction switching valve that allows either one of the pressurizing chamber and the liquid feeding chamber to communicate with a second communication port provided at the other end of the channel of the reaction processing vessel. The reaction processor may further include a control unit that controls the first direction switching valve and the second direction switching valve in order to move the sample inside the channel.

Another embodiment of the present invention relates to a reaction processing method. This method includes: placing a reaction processing vessel that is provided with a channel into which a sample is introduced; controlling the temperature of the channel in order to heat the sample inside the channel; and controlling the pressure inside the channel of the reaction processing vessel in order to move the sample inside the channel. The pressure inside the channel is maintained to be higher than the air pressure in the surrounding environment of the reaction processor, preferably 1 atm or higher, during a reaction process of the sample.

BRIEF DESCRIPTION OF THE DRAWINGS

Embodiments will now be described, by way of example only, with reference to the accompanying drawings which are meant to be exemplary, not limiting, and wherein like elements are numbered alike in several Figures, in which.

DETAILED DESCRIPTION OF THE INVENTION

Figure 1A:
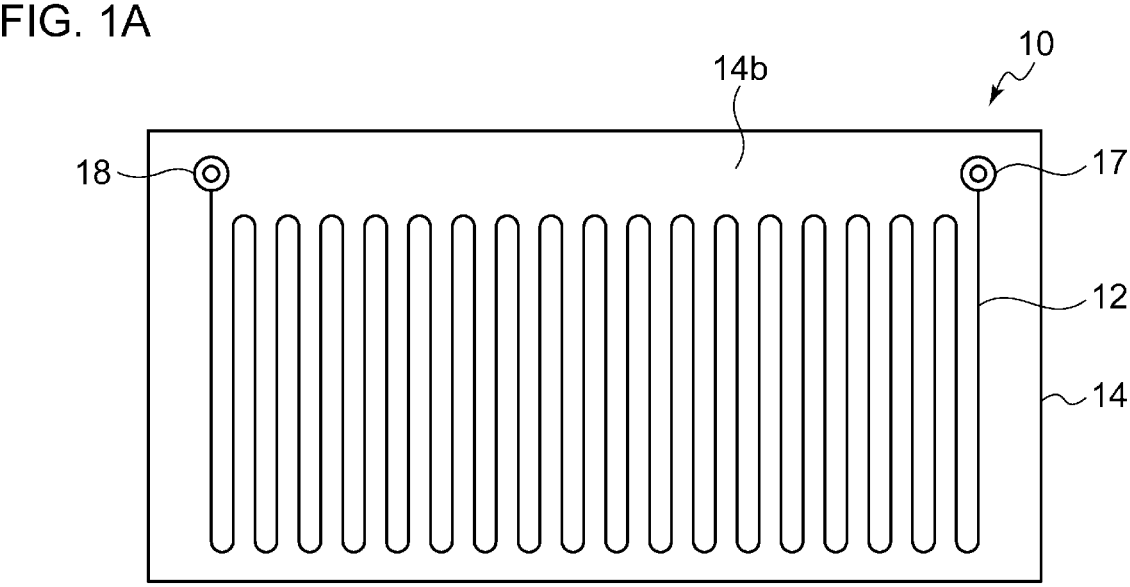
FIGS. 1A and 1B are diagrams for explaining a reaction processing vessel usable in a reaction processor according to a first embodiment of the present invention.

An explanation will be given in the following regarding a reaction processor according to an embodiment of the present invention. This reaction processor is a device for performing PCR. The same or equivalent constituting elements, members, and processes illustrated in each drawing shall be denoted by the same reference numerals, and duplicative explanations will be omitted appropriately. Reference herein to details of the illustrated embodiments is not intended to limit the scope of the claims. It should be understood that not all of the features and the combination thereof discussed are essential to the invention.

First Embodiment

Figure 1B:
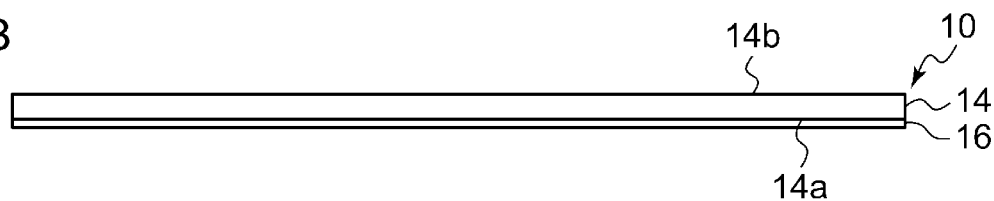

FIGS. 1A and 1B are diagrams for explaining a reaction processing vessel 10 usable in a reaction processor according to a first embodiment of the present invention. FIG. 1A is a plan view of the reaction processing vessel 10, and FIG. 1B is a front view of the reaction processing vessel 10.

As shown in FIGS. 1A and 1B, the reaction processing vessel 10 comprises a substrate 14 and a channel sealing film 16.

The substrate 14 is preferably formed of a material that is stable under temperature changes and is resistant to a sample solution that is used. Further, the substrate 14 is preferably formed of a material that has good moldability, a good transparency and barrier property, and a low self-fluorescence property. As such a material, an inorganic material such as glass, silicon (Si), or the like, a resin such as acrylic, polyester, silicone, or the like, and particularly cycloolefin are preferred. An example of the dimensions of the substrate 14 includes a long side of 70 mm, a short side of 42 mm, and a thickness of 3 mm.

A groove-like channel 12 is formed on the lower surface 14a of the substrate 14, and this channel 12 is sealed by the channel sealing film 16. The channel 12 is formed in a so-called serpiginous manner where a turn is continuously made by combining curved (turn) portions and straight portions in a plan view. Specifically, a combination of a pair of turn portions on respective sides (corresponding to a high temperature region and a low temperature region to be described later) and two straight portions (corresponding to a medium temperature region to be described later) connecting the pair of turn portions is defined as one unit, and units are formed in a continuous manner such that the number of the units is equal to or more than the scheduled number of thermal cycles to be applied to the sample. An example of the dimensions of the channel 12 formed on the lower surface 14a of the substrate 14 includes a width of 0.7 mm and a depth of 0.7 mm. A first communication port 17, which communicates with the outside, is formed at the position of one end of the channel 12 in the substrate 14. A second communication port 18 is formed at the position of the other end of the channel 12 in the substrate 14. The pair, the first communication port 17 and the second communication port 18, formed on the respective ends of the channel 12 is formed so as to be exposed on the upper surface 14b of the substrate 14. Such a substrate can be produced by injection molding or cutting work with an NC processing machine or the like.

On the lower surface 14a of the substrate 14, the channel sealing film 16 is attached. In the reaction processing vessel 10 according to the first embodiment, most of the channel 12 is formed in the shape of a groove exposed on the lower surface 14a of the substrate 14. This is for allowing for easy molding by injection molding using a metal mold or the like. In order to seal this groove so as to make use of the groove as a channel, the channel sealing film 16 is attached on the lower surface 14a of the substrate 14.

The channel sealing film 16 may be sticky on one of the main surfaces thereof or may have a functional layer that exhibits stickiness or adhesiveness by pressing that is formed on one of the main surfaces. Thus, the channel sealing film 16 has a function of being easily able to become integral with the lower surface 14a of the substrate 14 while being in close contact with the lower surface 14a. The channel sealing film 16 is desirably formed of a material, including an adhesive, that has a low self-fluorescence property. In this respect, a transparent film made of a resin such as a cycloolefin polymer, polyester, polypropylene, polyethylene or acrylic is suitable but is not limited thereto. Further, the channel sealing film 16 may be formed of a plate-like glass or resin. Since rigidity can be expected in this case, the channel sealing film 16 is useful for preventing warpage and deformation of the reaction processing vessel 10.

Figure 2:
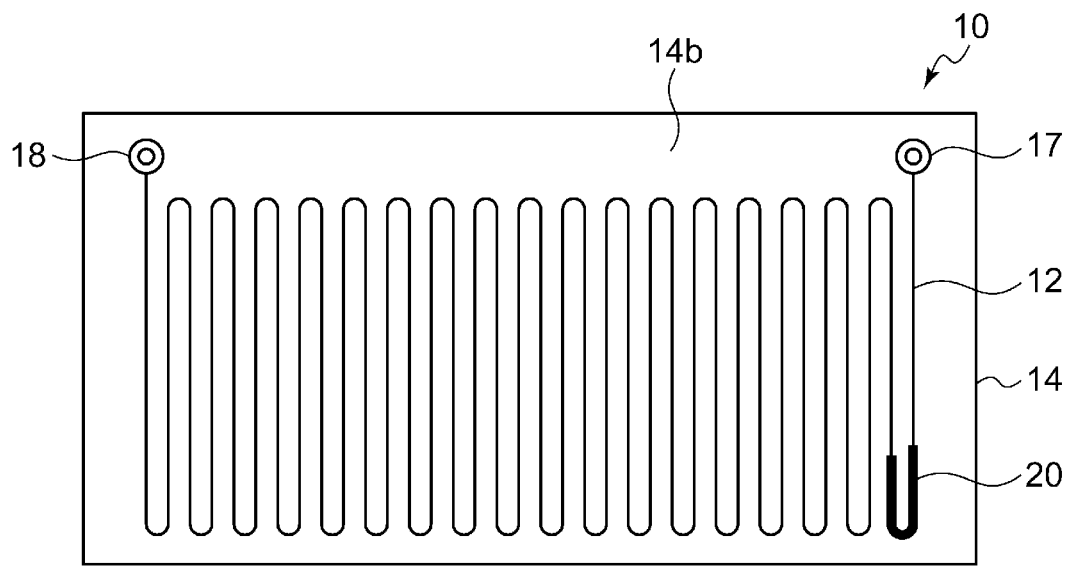
FIG. 2 is a diagram schematically showing a state where a sample is introduced into a channel of the reaction processing vessel.

FIG. 2 schematically shows a state where a sample 20 is introduced into the channel 12 of the reaction processing vessel 10. In FIG. 2, in order to emphasize the position of the sample 20, the sample 20 is shown by a solid line that is thicker than that for the channel 12. It should be noted that the solid line does not indicate a state where the sample 20 overflows outside the channel.

Figure 4:
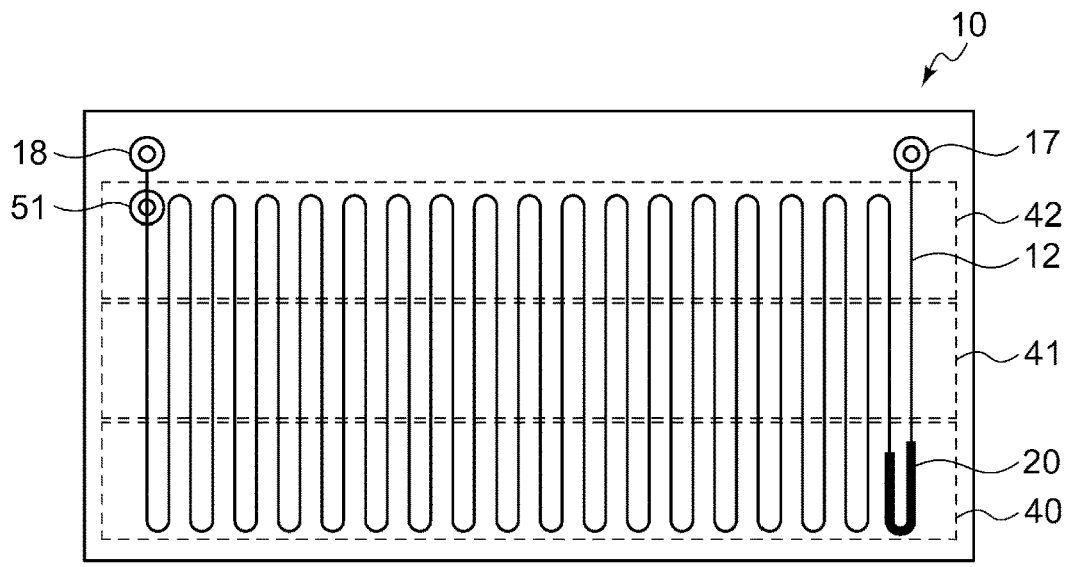
FIG. 4 is a diagram for explaining a state where the reaction processing vessel is set at a predetermined position of the reaction processor.

The sample 20 is introduced into the channel 12 through either one of the first communication port 17 and the second communication port 18. The method for the introduction is not limited to this. Alternatively, for example, an appropriate amount of sample may be directly introduced through the communication port using a pipette, a dropper, a syringe, or the like. Alternatively, a method of introduction may be used that is performed while preventing contamination via a cone-shaped needle chip, in which a filter made of porous PTFE or polyethylene is incorporated. In general, many types of such needle chips are sold and can be obtained easily, and the needle chips can be used while being attached to the tip of a pipette, a dropper, a syringe, or the like. Furthermore, the sample may be moved to a predetermined position in the channel as shown in FIG. 2 by discharging and introducing the sample by a pipette, a dropper, a syringe, or the like and then further pushing the sample through pressurization. Regarding the so-called initial position of the sample, as shown in FIG. 4, an example is shown where a position in the high temperature region 40 described later is set as the initial position. However, the initial position is not limited thereto.

The sample 20 includes, for example, those obtained by adding a plurality of types of primers, a thermostable enzyme and four types of deoxyribonucleoside triphosphates (dATP, dCTP, dGTP, dTTP) as PCR reagents to a mixture containing two or more types of DNA. Further, a fluorescent probe that specifically reacts to DNA subjected to a reaction process is mixed. Commercially available real-time PCR reagent kits and the like can be also used.

Figure 3:
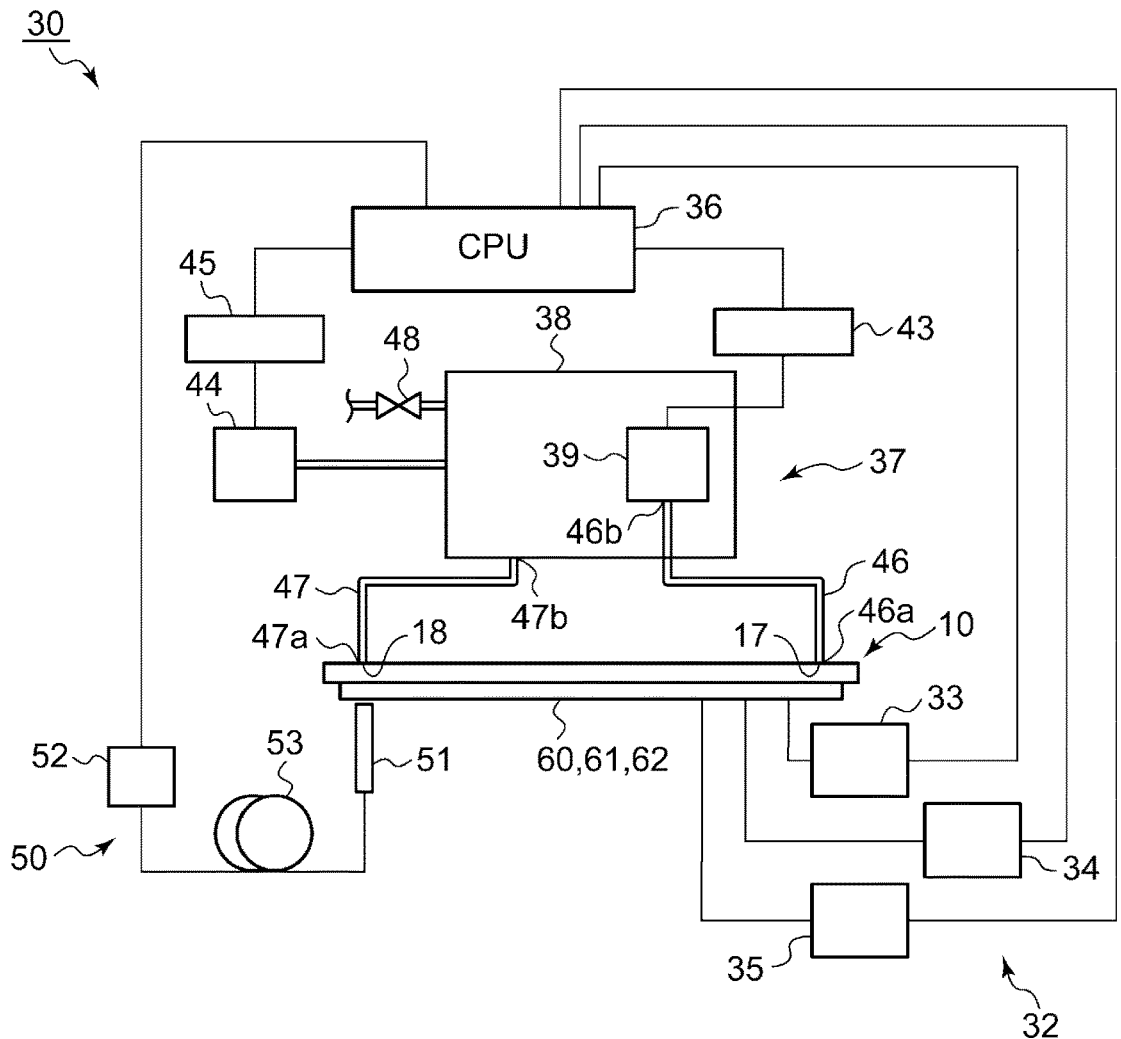
FIG. 3 is a schematic diagram for explaining the reaction processor according to the first embodiment of the present invention.

FIG. 3 is a schematic diagram for explaining a reaction processor 30 according to the first embodiment of the present invention. FIG. 4 is a diagram for explaining a state where the reaction processing vessel 10 is set at a predetermined position of the reaction processor 30.

The reaction processor 30 according to the first embodiment is provided with a reaction processing vessel placing portion (not shown) on which the reaction processing vessel 10 is placed, a temperature control system 32, and a CPU 36. As shown in FIG. 4, the temperature control system 32 is configured so as to be able to accurately maintain and control the temperature of a region 40, which is approximately the lower one third of the figure page in the channel 12 of the reaction processing vessel 10 placed on the reaction processing vessel placing portion, the temperature of a region 42, which is approximately the upper one third of the figure page, and the temperature of a region 41, which is approximately the middle one third of the figure page, to be three levels of temperature of about 95° C., about 55° C., and about 72° C., respectively. Hereinafter, the region 40 of the channel 12 is referred to as "high temperature region 40", the region 41 of the channel 12 is referred to as "medium temperature region 41", and the region 42 of the channel 12 is referred to as "low temperature region 42", and the regions are collectively referred to as a thermal cycle region.

The temperature control system 32 is for maintaining the temperature of each temperature region of the thermal cycle region and is specifically provided with a high temperature heater 60 for heating the high temperature region 40 of the channel 12, a medium temperature heater 61 for heating the medium temperature region 41 of the channel 12, a low temperature heater 62 for heating the low temperature region 42 of the channel 12, a temperature sensor (not shown) such as, for example, a thermocouple or the like for measuring the actual temperature of each temperature region, a high temperature heater driver 33 for controlling the temperature of the high temperature heater 60, a medium temperature heater driver 34 for controlling the temperature of the medium temperature heater 61, a low temperature heater driver 35 for controlling the temperature of the low temperature heater 62. Information on the actual temperature measured by the temperature sensor is sent to the CPU 36. Based on the information on the actual temperature of each temperature region, the CPU 36 controls each heater driver such that the temperature of each heater becomes a predetermined temperature. Each heater may be, for example, a resistance heating element, a Peltier element, or the like. The temperature control system 32 may be further provided with other components for improving the temperature controllability of each temperature region.

The reaction processor 30 according to the first embodiment is further provided with a liquid feeding system 37 for moving the sample 20 inside the channel 12 of the reaction processing vessel 10. By controlling the pressure inside the channel 12 using this liquid feeding system 37, the sample 20 is continuously moved in one direction inside the channel 12 such that the sample 20 can pass through each temperature region inside the thermal cycle region of the reaction processing vessel 10, and, as a result, a thermal cycle can be applied to the sample 20. More specifically, target DNA in the sample 20 is selectively amplified by applying a step of denaturation in the high temperature region 40, a step of annealing in the low temperature region 42, and a step of elongation in the medium temperature region 41. In other words, the high temperature region 40 can be considered to be a denaturation temperature region, the low temperature region 42 can be considered to be an annealing temperature region, and the medium temperature region 41 can be considered to be an elongation temperature region. The period of time for staying in each temperature region can be appropriately set by changing the period of time during which the sample stops at a predetermined position in each temperature region, the speed at which the sample moves, the size (area) of each temperature region, a channel length corresponding to each temperature region, and the like. Further, the annealing temperature region and the elongation temperature region may be combined into an annealing and elongation temperature region. In this case, the thermal cycle region is formed of temperature regions of two levels: a high temperature region for denaturation; and a temperature region (medium-low temperature region) where the temperature is lower than that of the high temperature region.

The liquid feeding system 37 is provided with a pressurizing chamber 38, a liquid feeding pump 39, a liquid feeding pump driver 43 for controlling the liquid feeding pump 39, a pressurizing chamber pump 44, a pressurizing chamber pump driver 45 for controlling the pressurizing chamber pump 44, a first tube 46, and a second tube 47.

A first end portion 46a of the first tube 46 is connected to the first communication port 17 of the reaction processing vessel 10. A packing material or a seal for securing airtightness is preferably arranged at the connection between the first communication port 17 and the first end portion 46a of the first tube 46. A second end portion 46b of the first tube 46 is connected to the output of the liquid feeding pump 39. The liquid feeding pump 39 may be, for example, a micro blower pump comprising a diaphragm pump.

The CPU 36 controls the air supply and pressurization from the liquid feeding pump 39 via the liquid feeding pump driver 43. The air supply and pressurization from the liquid feeding pump 39 act on the sample 20 inside the channel 12 through the first communication port 17 and becomes a propulsive force to move the sample 20.

As the liquid feeding pump 39, for example, a micro blower pump (MZB1001 T02 model) manufactured by Murata Manufacturing Co., Ltd., or the like can be used. While this micro blower pump can increase the pressure on a secondary side to be higher than a primary side during operation, the pressure on the primary side and the pressure on the secondary side become equal at the moment when the pump is stopped or when the pump is stopped. In the first embodiment, the liquid feeding pump 39 is entirely arranged inside the pressurizing chamber 38.

A first end portion 47a of the second tube 47 is connected to the second communication port 18 of the reaction processing vessel 10. A packing material or a seal for securing airtightness is preferably arranged at the connection between the second communication port 18 and the first end portion 47a of the second tube 47. A second end portion 47b of the second tube 47 is connected so as to communicate with the inside of the pressurizing chamber 38. As a result, the second communication port 18 of the reaction processing vessel 10 communicates with the atmosphere inside the pressurizing chamber 38.

The pressurizing chamber 38 forms a space having a certain volume therein. The pressurizing chamber pump 44 is connected to the pressurizing chamber 38. The pressurizing chamber pump driver 45 controls the pressurizing chamber pump 44 such that the space inside the pressurizing chamber 38 has a predetermined pressure in accordance with an instruction from the CPU 36. As the pressurizing chamber pump 44, for example, a compact DC diaphragm pump (DSA-1-12BL model) manufactured by Denso Sangyo Co., Ltd., or the like can be used, and a means of pressurization by a rubber ball, a syringe, or the like can be also used as a simple means. In the first embodiment, the pressure inside the pressurizing chamber 38 is set to be higher than the air pressure in the surrounding environment of the reaction processor 30 during the reaction process and more preferably maintained at 1 atm (1013 hPa) or higher. The air pressure in the surrounding environment of the reaction processor means the pressure (or atmospheric pressure) at a place where the reaction processor according to the present invention is installed, a place where the reaction process is performed by the processor, or, when the reaction processor is installed at a place that is partitioned from the surroundings, the partitioned place. The pressure inside the pressurizing chamber 38 needs to be applied to such an extent that significant evaporation of the sample and generation of air bubbles or the like, which affect a PCR reaction process, can be prevented even when the sample is repeatedly exposed to a high temperature (about 95° C.). The higher the pressure inside the pressurizing chamber 38 becomes, the more the influence of the evaporation of the sample and the like can be suppressed. However, on the other hand, the liquid feeding system 37 becomes complicated or enlarged including the handling thereof. Thus, a person skilled in the art can comprehensively judge the application, purpose, cost, effect, etc., of the processor so as to design the entire system.

An atmospheric pressure releasing valve 48 is provided in the pressurizing chamber 38. The atmospheric pressure releasing valve 48 is controlled such that the pressure of the liquid feeding system 37 (the inside of the pressurizing chamber 38, the first tube 46, the second tube 47, etc.) and the pressure in the channel 12 of the reaction processing vessel 10 become equal to the air pressure in the surrounding environment of the reaction processor 30 at the time of installing or removing the reaction processing vessel 10 in or from the reaction processor 30. Thereby, rapid movement and squirting of the sample 20 can be prevented.

Further, a pressure sensor (not shown) for constantly monitoring the pressure of the internal space thereof may be provided in the pressurizing chamber 38. By sending the actual pressure detected by the pressure sensor to the CPU 36, the pressure inside the pressurizing chamber 38 can be suitably controlled.

The reaction processor 30 according to the first embodiment is further provided with a fluorescence detector 50. Fluorescence from the sample 20 in the channel 12 of the reaction processing vessel 10 can be detected using the fluorescence detector 50, and the value thereof can be used as an index serving as information for determining the progress of the PCR or the termination of the reaction.

As the fluorescence detector 50, an optical fiber-type fluorescence detector FLE-510 manufactured by Nippon Sheet Glass Co., Ltd., can be used, which is a very compact optical system that allows for rapid measurement and the detection of fluorescence regardless of whether the place is a lighted place or a dark place. This optical fiber-type fluorescence detector allows the wavelength characteristic of the excitation light/fluorescence to be tuned such that the wavelength characteristic is suitable for the characteristic of fluorescence emitted from the sample 20 and thus allows an optimum optical and detection system for a sample having various characteristics to be provided.

The optical fiber-type fluorescence detector 50 is provided with an optical head 51, a fluorescence detector driver 52, and an optical fiber 53 connecting the optical head 51 and the fluorescence detector driver 52. The fluorescence detector driver 52 includes a light source for excitation light (LED, laser or other light sources adjusted to emit specific wavelengths), an optical fiber-type multiplexer/demultiplexer and a photoelectric conversion device (PD, APD, or a light detector such as a photomultiplier) (neither of which is shown), and a driver or the like for controlling these. The optical head 51 is formed of an optical system such as a lens and has a function of directionally irradiating the sample with excitation light and collecting fluorescence emitted from the sample. The collected fluorescence is separated from the excitation light by the optical fiber-type multiplexer/demultiplexer inside the fluorescence detector driver 52 through the optical fiber 53 and converted into an electric signal by the photoelectric conversion element. For example, as shown in FIG. 4, the optical head 51 may be arranged near the second communication port 18 of the reaction processing vessel 10. In this case, the completion of the amplification of DNA can be learned by detecting the fluorescence from the sample 20 sent near the second communication port 18 after the completion of the series of reaction processes. Further, a plurality of optical heads 51 may be arranged so as to be able to detect fluorescence from the sample 20 near the first communication port 17 or in the channel 12 along the way. By monitoring a change in the fluorescence signal along the channel 12, the amplification of the DNA can be known in a time series manner. The fluorescence detector is not limited to an optical fiber-type fluorescence detector as long as the fluorescence detector exhibits the function of detecting fluorescence from a sample.

A description will be given of a reaction processing method in which the reaction processor 30 configured as described above is used. In the initial state of the processor, it is assumed that the second end portion 46b of the first tube 46 is connected to the output of the liquid feeding pump 39 and that the first end portion 46a of the first tube 46 is open.

Further, it is assumed that the second end portion 47b of the second tube 47 is connected to the pressurizing chamber 38 and that the first end portion 47a of the second tube 47 is open.

First, the sample 20 is introduced into the reaction processing vessel 10 and moved to the initial position, and then the reaction processing vessel 10 is set on the reaction processing vessel placing portion of the reaction processor 30.

Next, the atmospheric pressure releasing valve 48 provided in the pressurizing chamber 38 is opened such that the respective pressures in the pressurizing chamber 38 and in the first tube 46 and the second tube 47 to be connected respectively to the first communication port 17 and the second communication port 18 of the reaction processing vessel 10 become equal to the atmospheric pressure. Subsequently, the first end portion 46a of the first tube 46 extending from the liquid feeding pump 39 is connected to the first communication port 17 of the reaction processing vessel 10, and the first end portion 47a of the second tube 47 extending from the pressurizing chamber 38 is connected to the second communication port 18 of the reaction processing vessel 10. Neither the liquid feeding pump 39 nor the pressurizing chamber pump 44 is operated at this point. Subsequently, the atmospheric pressure releasing valve 48 provided in the pressurizing chamber 38 is closed.

Next, the pressurizing chamber pump 44 is operated such that the pressure inside the pressurizing chamber 38 and in the channel 12 of the reaction processing vessel 10 communicating with the pressurizing chamber 38 is higher than the air pressure in the surrounding environment of the reaction processor 30, preferably 1 atm (1013 hPa) or higher. Since the liquid feeding pump 39 is not operated at this time, the pressure on the primary side and the pressure on the secondary side are equal, that is, the pressure of the first communication port 17 communicating with the secondary side of the liquid feeding pump 39 is also equal to the pressure inside the pressurizing chamber 38. Therefore, since the pressures in the spaces on respective sides (the first communication port 17 side and the second communication port 18 side) of the sample 20 in the channel 12 of the reaction processing vessel 10 are equal, the sample 20 does not move. Since the pressure in the sample 20 and the pressure inside the channel 12 including the sample 20 are higher than the air pressure in the surrounding environment of the reaction processor 30 and are preferably 1 atm or higher, even under a low atmospheric pressure environment such as a high altitude place, the boiling and foaming of the sample 20 caused due to the lowering of the boiling point of the sample 20 mainly composed of an aqueous solution can be prevented.

Subsequently, the temperature control system 32 is operated so as to start the temperature control of each temperature region in the reaction processing vessel 10. The temperature control may be put on hold for a predetermined amount of time until the temperature in each temperature region is stabilized. The temperature control is preferably started after the pressure inside the channel 12 is stabilized by the liquid feeding system 37.

Next, the liquid feeding pump 39 is operated by the liquid feeding pump driver 43. Thereby, the pressure inside the channel 12 on the first communication port 17 side becomes higher than that on the second communication port 18 side in the channel 12 on both sides of the sample 20, and the sample 20 can thus move toward the second communication port 18 while being pushed inside the channel 12. The sample 20 cyclically and continuously passes through each temperature region of the denaturation region (high temperature region 40), the annealing region (low temperature region 42), and the elongation region (medium temperature region 41) along the continuous serpentine channel 12. Further, in the case of a reaction processor in which temperature regions of two levels are set, the sample 20 cyclically and continuously passes through each temperature region of the denaturation region (high temperature region) and the annealing and elongation region (medium-low temperature region). This allows a predetermined number of thermal cycles to be applied to the sample 20 and allows PCR to occur such that predetermined DNA can be selectively amplified.

As described above, in the reaction processor 30 according to the first embodiment, the pressure inside the channel 12 of the reaction processing vessel 10 is always maintained to be higher than the air pressure in the surrounding environment of the reaction processor 30, preferably 1 atm or higher, during the reaction process. In other words, during the reaction process, the sample 20 is constantly pressurized to have a pressure higher than the air pressure in the surrounding environment of the reaction processor 30, preferably 1 atm or higher. Therefore, PCR can be performed while preventing the boiling of a sample and the generation of air bubbles even in a place where the air pressure is low such as a high altitude place or the inside of an airplane.

Second Embodiment

Figure 5A:
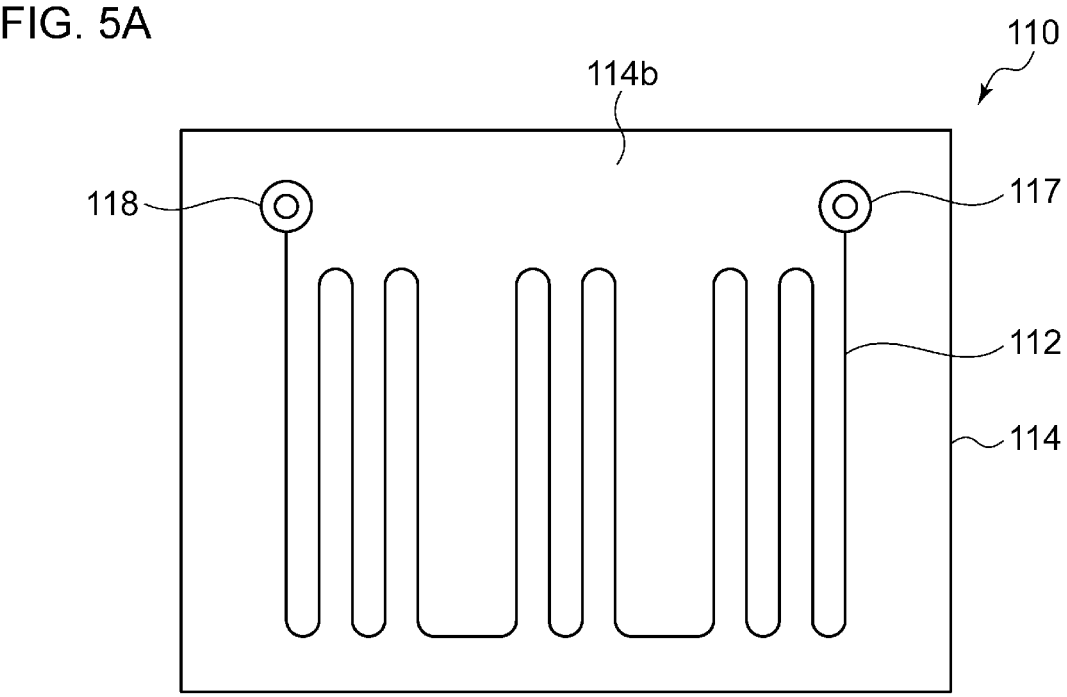
FIGS. 5A and 5B are diagrams for explaining a reaction processing vessel usable in a reaction processor according to a second embodiment of the present invention.
Figure 5B:
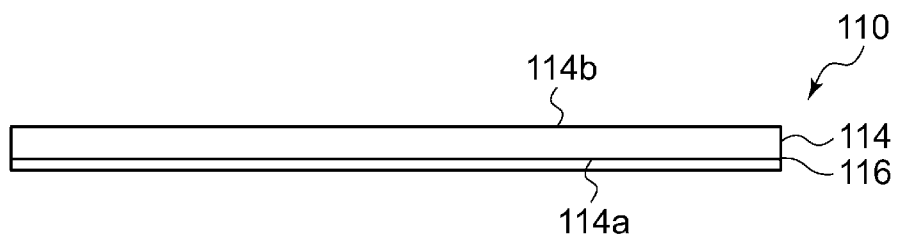

FIGS. 5A and 5B are diagrams for explaining a reaction processing vessel 110 usable in a reaction processor according to a second embodiment of the present invention. FIG. 5A is a plan view of the reaction processing vessel 110, and FIG. 5B is a front view of the reaction processing vessel 110.

As shown in FIGS. 5A and 5B, the reaction processing vessel 110 comprises a substrate 114 and a channel sealing film 116. The respective structures such as materials, dimensions, and the like of the substrate 114 and the channel sealing film 116 are the same as those of the reaction processing vessel 10 explained in the first embodiment. A groove-like channel 112 is formed on the lower surface 114a of the substrate 114, and this channel 112 is sealed by the channel sealing film 116. An example of the dimensions of the channel 112 formed on the lower surface 114a of the substrate 114 includes a width of 0.7 mm and a depth of 0.7 mm. A first communication port 117, which communicates with the outside, is formed at the position of one end of the channel 112 in the substrate 114. A second communication port 118 is formed at the position of the other end of the channel 112 in the substrate 114. The pair, the first communication port 117 and the second communication port 118, formed on the respective ends of the channel 112 is formed so as to be exposed on the upper surface 114b of the substrate 114. On the lower surface 114a of the substrate 114, the channel sealing film 116 is attached. In the reaction processing vessel 110 according to the second embodiment, most of the channel 112 is formed in the shape of a groove exposed on the lower surface 114a of the substrate 114. This is for allowing for easy molding by injection molding using a metal mold or the like or by cutting work by an NC processing machine. In order to seal this groove so as to make use of the groove as a channel, the channel sealing film 116 is attached on the lower surface 114a of the substrate 114.

The reaction processing vessel 110 according to the second embodiment is provided with a temperature range, in which the control of temperatures of a plurality of levels is possible, in the channel 112 between a pair of communication ports just like the reaction processing vessel 10 according to the first embodiment. However, the reaction processing vessel 110 is different from the reaction processing vessel 10 according to the first embodiment in that the channel 112 is not a serpentine channel that is folded back in a continuous manner. As will be described later, this is because a sample is intended to be sent so as to continuously reciprocate between temperature regions, where temperatures of a plurality of levels are maintained, of at least one channel 112 instead of sending a sample in a one-way continuous flow to a serpentine channel that is folded back in a continuous manner as in the reaction processing vessel 10 according to the first embodiment. A portion of the channel 112 that corresponds to each temperature region in the channel 112 may have a serpentine shape (smaller compared to that according to the first embodiment) formed of a curved (turn) portion and a straight portion in the temperature region, and the temperature regions are connected by, for example, a short channel. Since the area and channel length of each temperature region can be made smaller than those of the first embodiment, it is relatively easy to reduce variations in temperature in each temperature region, and there is also an advantage that the entire channel length can be shortened such that the reaction processing vessel and the reaction processor can be made small.

Figure 6:
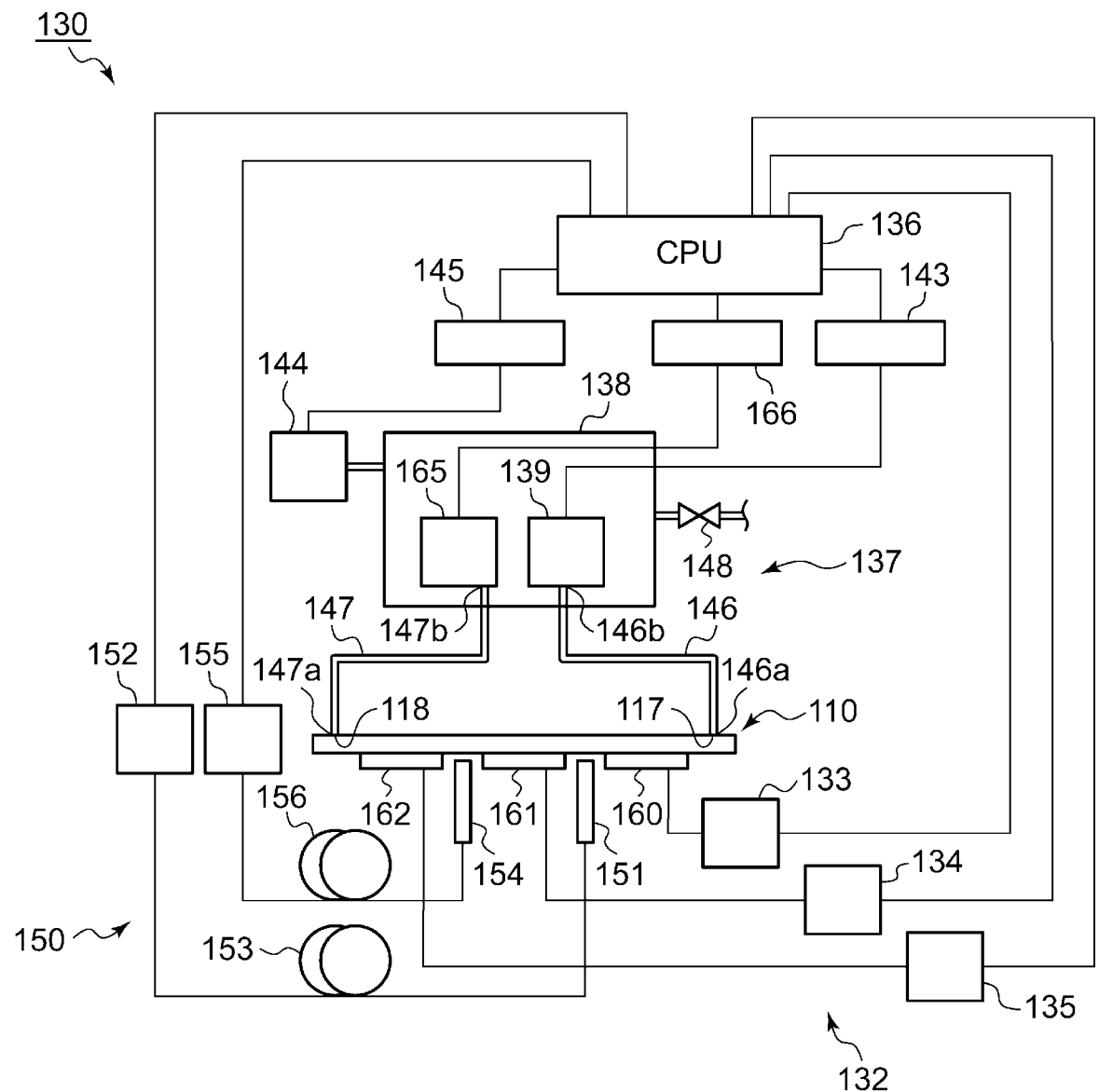
FIG. 6 is a schematic diagram for explaining the reaction processor according to the second embodiment of the present invention.
Figure 7:
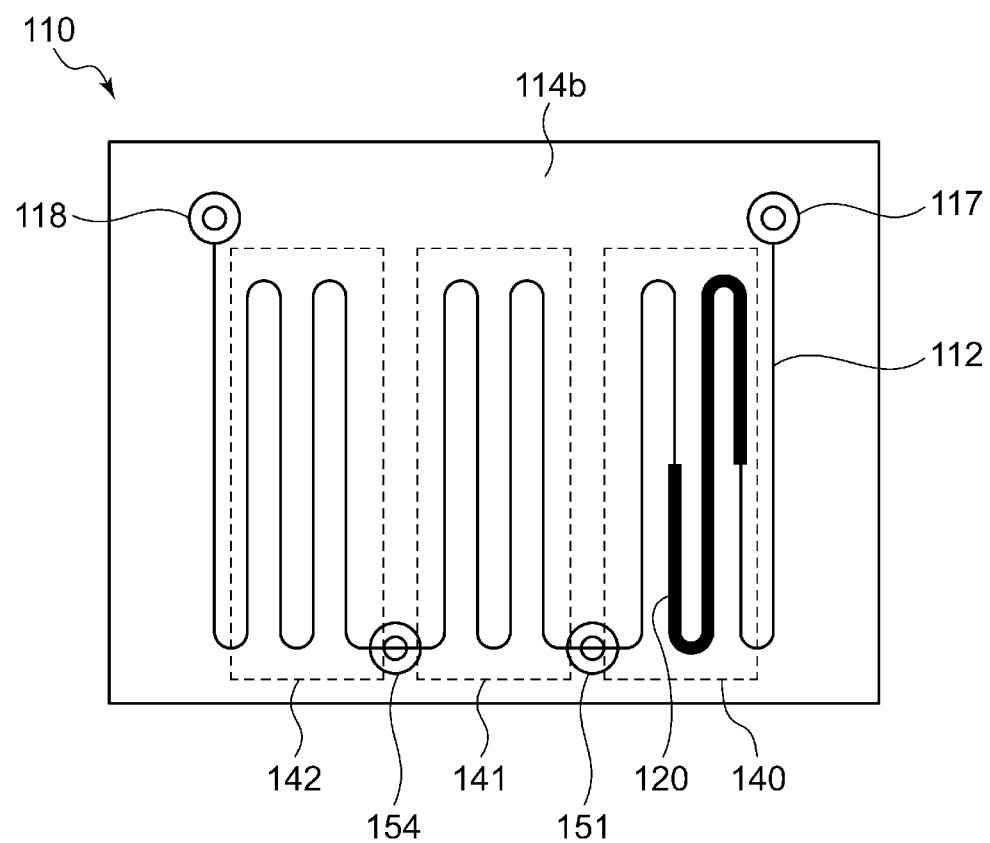
FIG. 7 is a diagram for explaining a state where the reaction processing vessel is set at a predetermined position of the reaction processor.

FIG. 6 is a schematic diagram for explaining a reaction processor 130 according to the second embodiment of the present invention. FIG. 7 is a diagram for explaining a state where the reaction processing vessel 110 is set at a predetermined position of the reaction processor 130. In FIG. 7, a sample 120 is introduced into the channel 112 of the reaction processing vessel 110. In FIG. 7, in the same way as in the first embodiment, in order to emphasize the position of the sample 120, the sample 120 is shown by a solid line that is thicker than that for the channel 112. It should be noted that the solid line does not indicate a state where the sample 120 overflows outside the channel. In the second embodiment, the sample 120, the method of introducing the sample 120, etc., are also the same as those in the first embodiment. Regarding the initial position of the sample 120, as shown in FIG. 7, an example is shown where a position in the high temperature region 140 described later is set as the initial position. However, the initial position is not limited thereto.

The reaction processor 130 according to the second embodiment is provided with a reaction processing vessel placing portion (not shown) on which the reaction processing vessel 110 is placed, a temperature control system 132, and a CPU 136. As shown in FIG. 7, the temperature control system 132 is configured so as to be able to accurately maintain and control the temperature of a region 140, which is approximately the right one third of the figure page in the channel 112 of the reaction processing vessel 110 placed on the reaction processing vessel placing portion, the temperature of a region 142, which is approximately the left one third of the figure page, and the temperature of a region 141, which is approximately the middle one third of the figure page, to be three levels of temperature of about 95° C., about 55° C., and about 72° C., respectively. Hereinafter, the region 140 of the channel 112 is referred to as "high temperature region 140", the region 141 of the channel 112 is referred to as "medium temperature region 141", and the region 142 of the channel 112 is referred to as "low temperature region 142", and the regions are collectively referred to as a thermal cycle region.

The temperature control system 132 is for maintaining each temperature region of the thermal cycle region and is specifically provided with a high temperature heater 160 for heating the high temperature region 140 of the channel 112, a medium temperature heater 161 for heating the medium temperature region 141 of the channel 112, a low temperature heater 162 for heating the low temperature region 142 of the channel 112, a temperature sensor (not shown) such as, for example, a thermocouple or the like for measuring the actual temperature of each temperature region, a high temperature heater driver 133 for controlling the temperature of the high temperature heater 160, a medium temperature heater driver 134 for controlling the temperature of the medium temperature heater 161, a low temperature heater driver 135 for controlling the temperature of the low temperature heater 162. Information on the actual temperature measured by the temperature sensor is sent to the CPU 136. Based on the information on the actual temperature of each temperature region, the CPU 136 controls each heater driver such that the temperature of each heater becomes a predetermined temperature. Each heater may be, for example, a resistance heating element, a Peltier element, or the like. The temperature control system 132 may be further provided with other components for improving the temperature controllability of each temperature region.

The reaction processor 130 according to the second embodiment is further provided with a liquid feeding system 137 for moving the sample 120 inside the channel 112 of the reaction processing vessel 110. By controlling the pressure inside the channel 112 using this liquid feeding system 137, the sample 120 is continuously moved inside the channel 112 in a reciprocating manner such that the sample 120 can pass through each temperature region inside the thermal cycle region of the reaction processing vessel 110, and, as a result, a thermal cycle can be applied to the sample 120. More specifically, target DNA in the sample 120 is selectively amplified by applying a step of denaturation in the high temperature region 140, a step of annealing in the low temperature region 142, and a step of elongation in the medium temperature region 141. In other words, the high temperature region 140 can be considered to be a denaturation temperature region, the low temperature region 142 can be considered to be an annealing temperature region, and the medium temperature region 141 can be considered to be an elongation temperature region. The period of time for staying in each temperature region can be appropriately set by changing the period of time during which the sample stops at a predetermined position in each temperature region, the speed at which the sample moves, the size (area) of each temperature region, a channel length corresponding to each temperature region, and the like. Further, the annealing temperature region and the elongation temperature region may be combined into an annealing and elongation temperature region. In this case, the thermal cycle region is formed of temperature regions of two levels: a high temperature region for denaturation; and a temperature region (medium-low temperature region) where the temperature is lower than that of the high temperature region.

The liquid feeding system 137 is provided with a pressurizing chamber 138, a first liquid feeding pump 139, a first liquid feeding pump driver 143 for controlling the first liquid feeding pump 139, a second liquid feeding pump 165, a second liquid feeding pump driver 166 for controlling the second liquid feeding pump 165, a pressurizing chamber pump 144, a pressurizing chamber pump driver 145 for controlling the pressurizing chamber pump 144, a first tube 146, and a second tube 147.

A first end portion 146a of the first tube 146 is connected to the first communication port 117 of the reaction processing vessel 110. A packing material or a seal for securing airtightness is preferably arranged at the connection between the first communication port 117 and the first end portion 146a of the first tube 146. A second end portion 146b of the first tube 146 is connected to the output of the first liquid feeding pump 139. The first liquid feeding pump 139 may be, for example, a micro blower pump comprising a diaphragm pump. In the same way, a first end portion 147a of the second tube 147 is connected to the second communication port 118 of the reaction processing vessel 110. A packing material or a seal for securing airtightness is preferably arranged at the connection between the second communication port 118 and the first end portion 147a of the second tube 147. A second end portion 147b of the second tube 147 is connected to the output of the second liquid feeding pump 165. The second liquid feeding pump 165 may be, for example, a micro blower pump comprising a diaphragm pump.

The CPU 136 controls the air supply and pressurization from the first liquid feeding pump 139 and the second liquid feeding pump 165 via the first liquid feeding pump driver 143 and the second liquid feeding pump driver 166. The air supply and pressurization from the first liquid feeding pump 139 and the second liquid feeding pump 165 act on the sample 120 inside the channel 112 through the first communication port 117 and the second communication port 118 and becomes a propulsive force to move the sample 120.

As the first liquid feeding pump 139 and the second liquid feeding pump 165, for example, a micro blower pump (MZB1001 T02 model) manufactured by Murata Manufacturing Co., Ltd., or the like can be used. In the second embodiment, the first liquid feeding pump 139 and the second liquid feeding pump 165 are both entirely arranged inside the pressurizing chamber 138.

The pressurizing chamber 138 forms a space having a certain volume therein. A pressurizing chamber pump 144 is connected to the pressurizing chamber 138. The pressurizing chamber pump driver 145 controls the pressurizing chamber pump 144 such that the space inside the pressurizing chamber 138 has a predetermined pressure in accordance with an instruction from the CPU 136. As the pressurizing chamber pump 144, a compact DC diaphragm pump (DSA-1-12BL model) manufactured by Denso Sangyo Co., Ltd., or the like can be used, and a means of pressurization by a rubber ball, a syringe, or the like can be also used as a simple means. In the second embodiment, the pressure inside the pressurizing chamber 138 is set to be higher than the air pressure in the surrounding environment of the reaction processor 130 during the reaction process and more preferably maintained at 1 atm (1013 hPa) or higher. The pressure inside the pressurizing chamber 138 needs to be applied to such an extent that significant evaporation of the sample and generation of air bubbles or the like, which affect the PCR reaction process, can be prevented even when the sample is repeatedly exposed to a high temperature (about 95° C.). The higher the pressure inside the pressurizing chamber 138 becomes, the more the influence of the evaporation of the sample and the like can be suppressed. However, on the other hand, the liquid feeding system 137 becomes complicated or enlarged including the handling thereof. Thus, a person skilled in the art can comprehensively judge the application, purpose, cost, effect, etc., of the processor so as to design the entire system.

An atmospheric pressure releasing valve 148 is provided in the pressurizing chamber 138. The atmospheric pressure releasing valve 148 is controlled such that the pressure of the liquid feeding system 137 and the pressure of the reaction processing vessel 110 in the channel 112 become equal to the atmospheric pressure at the time of installing or removing the reaction processing vessel 110. Thereby, rapid movement and squirting of the sample 120 can be prevented.

Further, a pressure sensor (not shown) for constantly monitoring the pressure of the internal space thereof may be provided in the pressurizing chamber 138. By sending the actual pressure detected by the pressure sensor to the CPU 136, the pressure inside the pressurizing chamber 138 can be suitably controlled.

The reaction processor 130 according to the second embodiment is further provided with a fluorescence detector 150. Fluorescence from the sample 120 in the channel 112 of the reaction processing vessel 110 can be detected using the fluorescence detector 150, and the value thereof can be used as an index serving as information for determining the progress of the PCR or the termination of the reaction.

As the fluorescence detector 150, an optical fiber-type fluorescence detector can be used in the same way as in the first embodiment. The optical fiber-type fluorescence detector 150 is provided with a first optical head 151, a second optical head 154, a first fluorescence detector driver 152, a second fluorescence detector driver 155, a first optical fiber 153 connecting the first optical head 151 and the first fluorescence detector driver 152, and a second optical fiber 156 connecting the second optical head 154 and the second fluorescence detector driver 155. The combination of the first optical head 151, the first fluorescence detector driver 152, and the first optical fiber 153 can be also referred to as a first fluorescence detector, and the combination of the second optical head 154, the second fluorescence detector driver 155, and the second optical fiber 156 can be also referred to as a second fluorescence detector. Furthermore, a third fluorescence detector, a fourth fluorescence detector, and a higher-order fluorescence detector may be provided. For the first and second fluorescence detectors, those having the same structures as those according to the first embodiment can be used, respectively, and the detailed description thereof will be thus omitted. Further, the first and second fluorescence detectors may have the same characteristics (for example, the target wavelengths of excitation light and fluorescence are the same) or may have different characteristics (such as different target wavelengths). In this case, it is advantageous in that amplification of a plurality of types of DNA having different fluorescence characteristics can be known in some cases.

As shown in FIG. 7, the first optical head 151 is arranged in a channel connecting the high temperature region 140 and the medium temperature region 141. The second optical head 154 is arranged in a channel connecting the medium temperature region 141 and the low temperature region 142. Since the reaction progresses while the sample 120 is fed in a reciprocating manner in the channel 112 and predetermined DNA contained in the sample 120 is amplified, by monitoring a change in the amount of fluorescence obtained from the sample, the progress of the DNA amplification can be learned in real time. In a serpentine channel having a continuous flow moving in one direction according to the first embodiment, it is substantially difficult to check the progress of DNA amplification in real time. This is because it is necessary to appropriately install far more fluorescent detectors on a long channel compared to the number of fluorescent detectors according to the second embodiment and scan along the channel of the fluorescence detectors. The reaction processing vessel comprising a serpentine channel having a reciprocating flow according to the second embodiment is also advantageous in this point.

A description will be given of a reaction processing method in which the reaction processor 130 configured as described above is used. In the initial state of the processor, it is assumed that the second end portion 146b of the first tube 146 is connected to the output of the liquid feeding pump 139 and that the first end portion 146a of the first tube 146 is open. Also, it is assumed that the second end portion 147b of the second tube 147 is connected to the output of the second liquid feeding pump 165 and that the first end portion 147a of the second tube 147 is open.

First, the sample 120 is introduced into the reaction processing vessel 110 and moved to the initial position, and then the reaction processing vessel 110 is set on the reaction processing vessel placing portion of the reaction processor 130.

Next, the atmospheric pressure releasing valve 148 provided in the pressurizing chamber 138 is opened such that the respective pressures in the pressurizing chamber 138 and in the first tube 146 and the second tube 147 to be connected respectively to the first communication port 117 and the second communication port 118 of the reaction processing vessel 110 become equal to the atmospheric pressure. Subsequently, the first end portion 146a of the first tube 146 extending from the first liquid feeding pump 139 is connected to the first communication port 117 of the reaction processing vessel 110, and the first end portion 147a of the second tube 147 extending from the second liquid feeding pump 165 is connected to the second communication port 118 of the reaction processing vessel 110. None of the first liquid feeding pump 139, the second liquid feeding pump 165, and the pressurizing chamber pump 144 is operated at this point. Subsequently, the atmospheric pressure releasing valve 148 provided in the pressurizing chamber 138 is closed.

Next, the pressurizing chamber pump 144 is operated by the pressurizing chamber pump driver 145 such that the pressure inside the pressurizing chamber 138 and in the channel 112 of the reaction processing vessel 110 communicating with the pressurizing chamber 138 is higher than the air pressure in the surrounding environment of the reaction processor 130, preferably 1 atm (1013 hPa) or higher. Since neither the first liquid feeding pump 139 nor the second liquid feeding pump 165 is in operation at this time, the pressure on the primary side and the pressure on the secondary side are equal, that is, the pressure of the first communication port 117 on the secondary side and the pressure of the second communication port 118 are also equal to the pressure inside the pressurizing chamber 138. Therefore, since the pressures in the spaces on respective sides (the first communication port 117 side and the second communication port 118 side) of the sample 120 in the channel 112 of the reaction processing vessel 110 are equal, the sample 120 does not move. Since the pressure in the sample 120 and the pressure inside the channel 112 including the sample 120 are always higher than the air pressure in the surrounding environment of the reaction processor 130 and are preferably 1 atm or higher, even under a low atmospheric pressure environment such as a high altitude place, the boiling and foaming of the sample 120 caused due to the lowering of the boiling point of the sample 120 mainly composed of an aqueous solution can be prevented.

Subsequently, the temperature control system 132 is operated so as to start the temperature control of each temperature region in the reaction processing vessel 110. The temperature control may be put on hold for a predetermined amount of time until the temperature in each temperature region is stabilized. The temperature control is preferably started after the pressure inside the channel 112 is kept to be a certain pressure or higher by the liquid feeding system 137.

It is assumed that the initial position of the sample 120 is located, for example, in the high temperature region 140. When the sample 120 is in the high temperature region 140 for a certain period of time, denaturation of the DNA occurs. First, the first liquid feeding pump 139 is operated. Thereby, the pressure inside the channel 112 on the first communication port 117 side becomes higher than that on the second communication port 118 side in the spaces on both sides of the sample 120, and the sample 120 can thus move from the high temperature region 140 to the low temperature region 142 via the medium temperature region 141 while being pushed inside the channel 112 toward the second communication port 118. When the sample 120 reaches the low temperature region 142, the first liquid feeding pump 139 is stopped. When the first liquid feeding pump 139 is stopped, the pressure on the primary side and the pressure on the secondary side become equal as described above. Thus, the pressure in the space on the first communication port 117 side of the sample 120 and the pressure in the channel space on the second communication port 118 side of the sample 120 both become equal to the pressure inside the pressurizing chamber 138 (i.e., there is no difference), and the sample 120 thus stops moving. Placing the sample 120 in the low temperature region 142 for a certain period of time causes annealing of the DNA.

Subsequently, the second liquid feeding pump 165 is operated, and, when the movement of the sample 120 from the low temperature region 142 to the medium temperature region 141 is completed, the second liquid feeding pump 165 is stopped. Placing the sample 120 in the medium temperature region 141 for a certain period of time causes elongation of the DNA. Further, the second liquid feeding pump 165 is operated, and, when the movement of the sample 120 from the medium temperature region 141 to the high temperature region 140 is completed, the second liquid feeding pump 165 is stopped. Placing the sample 120 in the high temperature region 140 for a certain period of time causes denaturation of the DNA.

By controlling the operation of the liquid feeding system 137 so as to repeat the movement of the sample 120 described above, the sample 120 reciprocates inside the channel 112. More specifically, the sample 120 cyclically passes through the respective regions of the temperatures: a high temperature (denaturation); a low temperature (annealing); a medium temperature (elongation); a high temperature (denaturation); a low temperature (annealing); a medium temperature (elongation); and so on. Further, in the case of a reaction processor where temperature regions of two levels are set, the sample 120 cyclically passes through the respective regions of the temperatures: a high temperature (denaturation); a medium-low temperature (annealing and elongation); a high temperature (denaturation); a medium-low temperature (annealing and elongation); and so on. This allows a predetermined number of thermal cycles to be applied to the sample 120 and allows PCR to occur such that predetermined DNA can be selectively amplified.

In the reaction processor 130 according to the second embodiment, since the sample 120 continuously reciprocates inside a single channel 112 connecting a plurality of temperature regions, it is important to control the position of the sample 120. Therefore, the fluorescence detector 150 described above can be allowed to function as a position sensor. If the optical head of the fluorescence detector 150 is arranged so as to detect fluorescence emitted from the sample 120 at a specific location in the channel 112, a fluorescence signal is at zero or at a background level when the sample 120 is not at the specific location, and the fluorescence signal exhibits a change in output rising from zero or the background level and then going back to zero or the background level again when the sample 120 passes through the specific location. Therefore, based on the output of a fluorescence signal based on the passage of the sample 120, for example, by controlling the driver for driving the liquid feeding system 137, it is possible to perform the feeding of the sample 120 in a reciprocating manner accompanied by proper positioning of the sample 120. Further, a plurality of optical heads of the fluorescence detector 150 can be arranged along the channel 112. For example, by arranging an optical head of the fluorescence detector 150 immediately below each reaction region, the presence or absence of the sample 120 in each reaction region can be detected, thus allowing for more reliable positioning of the sample 120.

The reaction processing method in which the reaction processor 130 according to the second embodiment is used is advantageous in that, unlike the reaction processing method in which the reaction processor 30 is used according to the first embodiment, fluorescence from the sample 120 can be continuously detected even during the reaction process by means of the thermal cycle and the progress of DNA amplification can be managed in real time as described above.

As described above, in the reaction processor 130 according to the second embodiment, the pressure inside the channel 112 of the reaction processing vessel 110 is always maintained to be higher than the air pressure in the surrounding environment of the reaction processor 230, preferably 1 atm or higher, during the reaction process. In other words, during the reaction process, the sample 120 is constantly pressurized to have a pressure higher than the air pressure in the surrounding environment of the reaction processor 130, preferably 1 atm or higher. Therefore, stable PCR can be performed while preventing the boiling of a sample and the generation of air bubbles even in a place where the air pressure is low such as a high altitude place or the inside of an airplane.

Third Embodiment

Figure 8:
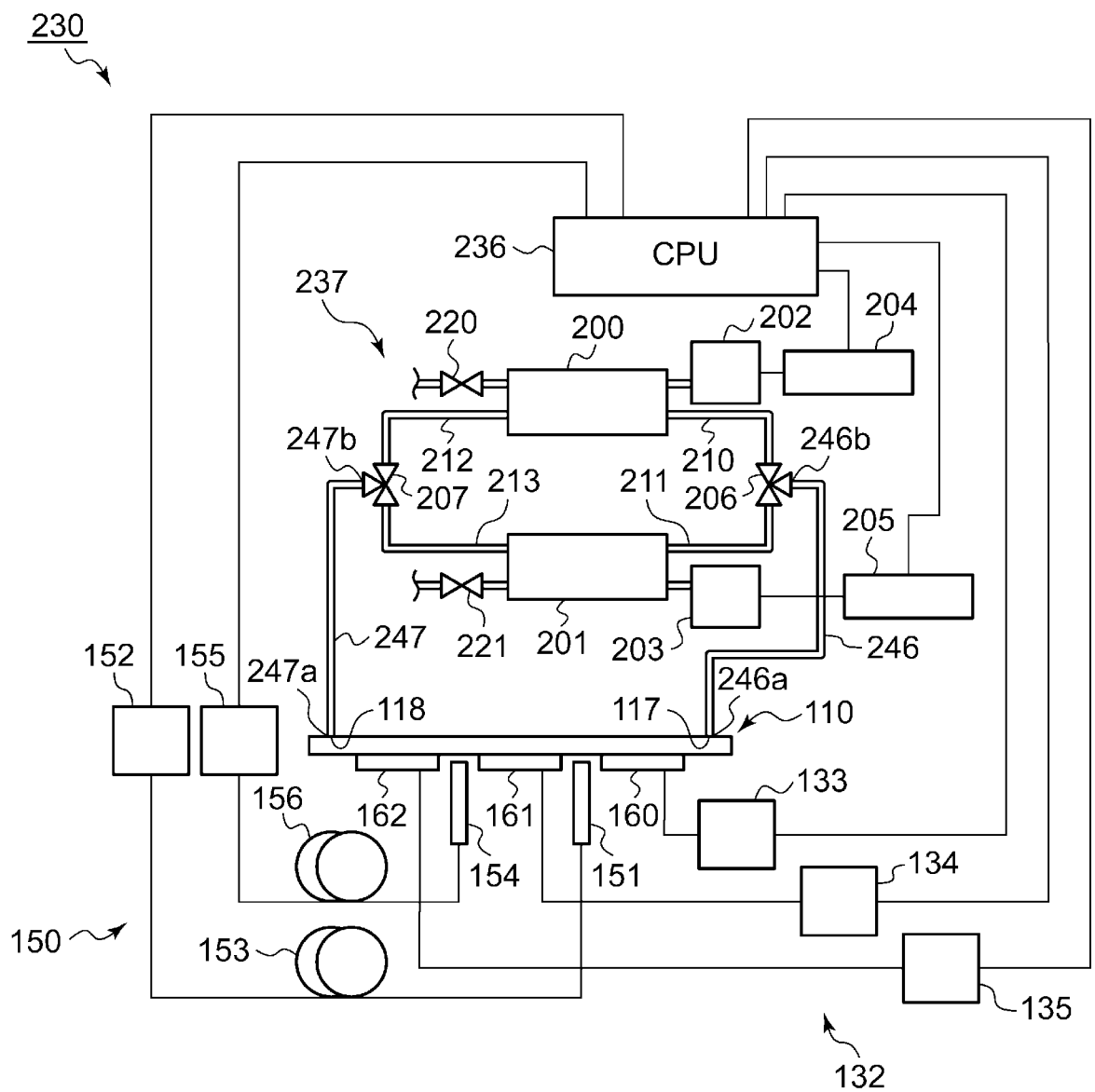
FIG. 8 is a schematic diagram for explaining a reaction processor according to a third embodiment of the present invention.

FIG. 8 is a schematic diagram for explaining a reaction processor 230 according to the third embodiment of the present invention. In the reaction processor 230 according to the third embodiment, since a reaction processing vessel that is the same as the reaction processing vessel 110 (see FIG. 5) described in the second embodiment is used, like numerals represent like constituting elements, and duplicative explanations will be omitted. Further, since a temperature control system and a fluorescence detector that are the same as the temperature control system 132 and the fluorescence detector 150 explained in the second embodiment are also used in the reaction processor 230, like numerals represent like constituting elements, and duplicative explanations will be omitted. In the reaction processor 230 according to the third embodiment of the present invention, the configuration of the liquid feeding system and the reaction processing method based thereon are different from those according to the second embodiment.

A liquid feeding system 237 of the reaction processor 230 according to the third embodiment of the present invention is provided with a liquid feeding chamber 200, a pressurizing chamber 201, a liquid feeding chamber pump 202, a liquid feeding chamber pump driver 204 for controlling the liquid feeding chamber pump 202, a pressurizing chamber pump 203, a pressurizing chamber pump driver 205 for controlling the pressurizing chamber pump 203, a first direction switching valve 206, a second direction switching valve 207, a first tube 246, and a second tube 247. Also, the reaction processor 230 may be provided with a driver (not shown) for controlling the first direction switching valve 206 and the second direction switching valve 207.

Figure 9:
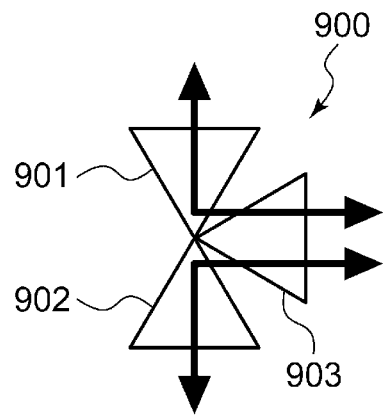
FIG. 9 is a schematic diagram for explaining the configuration of a direction switching valve.

FIG. 9 is a schematic diagram for explaining the configuration of a direction switching valve. The direction switching valve 900 shown in FIG. 9 can be used as the first direction switching valve 206 and the second direction switching valve 207 in the reaction processor 230 shown in FIG. 8. As shown in FIG. 9, the direction switching valve 900 is provided with a first supply port 901, a second supply port 902, and a discharge port 903. The direction switching valve 900 is capable of switching communication between the first supply port 901 and the discharge port 903 and communication between the second supply port 902 and the discharge port 903. A means for the switching of communication may be of a direct acting electromagnetic type or pilot electromagnetic type in which an internal valve is switched by a separate air pressure. Also, a so-called universal type valve may be used, which allows the air to flow bidirectionally in a path between the first supply port 901 and the discharge port 903 or a path between the second supply port 902 and the discharge port 903. Alternatively, a direction switching valve provided with four or more ports can be also used. Further, the direction switching valve is not limited to these and may be something like a three-way valve. Further, the valve may be provided with a structure that controls the rotation of the three-way cock with a stepping motor or the like.

Referring back to FIG. 8, a first end portion 246a of the first tube 246 is connected to the first communication port 117 of the reaction processing vessel 110. A packing material or a seal for securing airtightness is preferably arranged at the connection between the first communication port 117 and the first end portion 246a of the first tube 246. The second end portion 246b of the first tube 246 is connected to the discharge port of the first direction switching valve 206. Further, the first supply port of the first direction switching valve 206 is connected to the liquid feeding chamber 200 by a hollow tube 210. Further, the second supply port of the first direction switching valve 206 is connected to the pressurizing chamber 201 by a hollow tube 211.

In the same way, a first end portion 247a of the second tube 247 is connected to the second communication port 118 of the reaction processing vessel 110. A packing material or a seal for securing airtightness is preferably arranged at the connection between the second communication port 118 and the first end portion 247a of the second tube 247. The second end portion 247b of the second tube 247 is connected to the discharge port of the second direction switching valve 207. Further, the first supply port of the second direction switching valve 207 is connected to the liquid feeding chamber 200 by a hollow tube 212. Further, the second supply port of the second direction switching valve 207 is connected to the pressurizing chamber 201 by a hollow tube 213.

The liquid feeding chamber 200 forms a space having a certain volume therein. The liquid feeding chamber pump 202 is connected to the liquid feeding chamber 200. The liquid feeding chamber pump driver 204 controls the liquid feeding chamber pump 202 such that the space inside the liquid feeding chamber 200 has a predetermined pressure in accordance with an instruction from a CPU 236.

In the same way, the pressurizing chamber 201 forms a space having a certain volume therein. The pressurizing chamber pump 203 is connected to the pressurizing chamber 201. The pressurizing chamber pump driver 205 controls the pressurizing chamber pump 203 such that the space inside the pressurizing chamber 201 has a predetermined pressure in accordance with an instruction from the CPU 236.

As the liquid feeding chamber pump 202 and as the pressurizing chamber pump 203, a compact DC diaphragm pump (DSA-1-12BL model) manufactured by Denso Sangyo Co., Ltd., or the like can be used, and a means of pressurization by a rubber ball, a syringe, or the like can be also used as a simple means.

In the third embodiment, the pressure inside the liquid feeding chamber 200 and the pressure inside the pressurizing chamber 201 are set to be higher than the air pressure in the surrounding environment of the reaction processor 130 during the reaction process and more preferably maintained at 1 atm (1013 hPa) or higher. The pressure inside the liquid feeding chamber 200 is maintained to be higher than the pressure inside the pressurizing chamber 201 during the reaction process.

The liquid feeding chamber 200 and the pressurizing chamber 201 are provided with atmospheric pressure releasing valves 220 and 221, respectively. By the atmospheric pressure releasing valves 220 and 221, the pressure condition inside the chamber can be reset when the reaction processor 230 is repeatedly used such that sudden movement and squirting of the sample 120 at the time of installing or removing the reaction processing vessel 110 can be prevented.

A description will be given of a reaction processing method in which the reaction processor 230 configured as described above is used. In the initial state of the processor, it is assumed that the second end portion 246b of the first tube 246 is connected to the discharge port of the first direction switching valve 206 and that the first end portion 246a of the first tube 246 is open. Also, it is assumed that the second end portion 247b of the second tube 247 is connected to the discharge port of the second direction switching valve 207 and that the first end portion 247a of the second tube 247 is open.

First, the sample 120 is introduced into the reaction processing vessel 110 and moved to the initial position, and then the reaction processing vessel 110 is set on the reaction processing vessel placing portion of the reaction processor 230.

Next, the atmospheric pressure releasing valves 220 and 221 are opened such that the respective pressures in the liquid feeding chamber 200, the pressurizing chamber 201, the first direction switching valve 206, the second direction switching valve 207, the first tube 246, and the second tube 247 become equal to the atmospheric pressure. Subsequently, the first end portion 246a of the first tube 246 extending from the first direction switching valve 206 is connected to the first communication port 117 of the reaction processing vessel 110, and the first end portion 247a of the second tube 247 extending from the second direction switching valve 207 is connected to the second communication port 118 of the reaction processing vessel 110. Neither the liquid feeding chamber pump 202 nor the pressurizing chamber pump 203 is operated at this point. Subsequently, the atmospheric pressure releasing valves 220 and 221 are closed.

Next, after switching to the respective paths where the second supply ports communicating with the pressurizing chamber 201 communicate with the respective discharge ports by operating the first direction switching valve 206 and the second direction switching valve 207, the pressurizing chamber pump 203 is operated. The pressure in the pressurizing chamber 201 is increased to be higher than the air pressure in the surrounding environment of the reaction processor 130 and more preferably to be 1 atm (1013 hPa) or higher. The pressurizing chamber 201 communicates with the first communication port 117 and the second communication port 118 of the reaction processing vessel 110 via the respective second supply ports and the respective discharge ports of the first direction switching valve 206 and the second direction switching valve 207. Therefore, since the pressures on respective sides (the first communication port 117 side and the second communication port 118 side) of the sample 120 also become equal due to the increasing of the pressure in the pressurizing chamber 201, the pressure balance in the channel is not affected, and the sample 120 thus does not move.

Subsequently, the temperature control system 132 is operated so as to start the temperature control of each temperature region in the reaction processing vessel 110. The temperature control may be put on hold for a predetermined amount of time until the temperature in each temperature region is stabilized.

Subsequently, the liquid feeding chamber pump 202 is operated to raise the pressure inside the liquid feeding chamber 200. Since the liquid feeding chamber 200 does not communicate with the spaces on respective sides (the first communication port 117 side and the second communication port 118 side) of the sample 120 in the channel of the reaction processing vessel 110 at this point, the pressure in the channel is not affected by the increasing of the pressure in the liquid feeding chamber 200, and the sample 120 thus does not move. However, the pressure inside the liquid feeding chamber 200 is higher than the pressure inside the pressurizing chamber 201 as described above. This pressure difference serves as a propulsive force for moving the sample 120.

It is assumed that the initial position of the sample 120 is located, for example, in the high temperature region 140 shown in FIG. 7. When the sample 120 is in the high temperature region 140 for a certain period of time, denaturation of the DNA occurs. First, the first direction switching valve 206 is operated to switch to a path where the first supply port and the discharge port communicate with each other. Thereby, the pressure in the space on the first communication port 117 side of the sample 120 becomes equal to the pressure inside the liquid feeding chamber 200, and the pressure in the space on the first communication port 117 side becomes higher than the pressure on the second communication port 118 side. Thus, the sample 120 can move from the high temperature region 140 to the low temperature region 142 via the medium temperature region 141 while being pushed inside the channel 112 toward the second communication port 118. When the sample 120 reaches the low temperature region 142, the first direction switching valve 206 is operated to switch to a path where the second supply port and the discharge port communicate with each other. Thereby, the pressure in the space on the first communication port 117 side of the sample 120 becomes the same as the pressure inside the pressurizing chamber 201, and the pressure in the space on the first communication port 117 side becomes equal to the pressure on the second communication port 118 side. Thus, the sample 120 stops moving. Placing the sample 120 in the low temperature region 142 for a certain period of time causes annealing of the DNA.

Subsequently, the second direction switching valve 207 is operated to switch to a path where the first supply port and the discharge port communicate with each other. Thereby, the pressure in the space on the second communication port 118 side of the sample 120 becomes the same as the pressure inside the liquid feeding chamber 200, and the pressure in the space on the second communication port 118 side becomes higher than the pressure on the first communication port 117 side. Thus, the sample 120 can move from the low temperature region 142 to the medium temperature region 141 while being pushed inside the channel toward the first communication port 117. When the sample 120 reaches the medium temperature region 141, the second direction switching valve 207 is operated to switch to a path where the second supply port and the discharge port communicate with each other. Thereby, the pressure in the space on the second communication port 118 side of the sample 120 becomes the same as the pressure inside the pressurizing chamber 201, and the pressure in the space on the second communication port 118 side becomes equal to the pressure on the first communication port 117 side. Thus, the sample 120 stops moving. Placing the sample in the medium temperature region 141 for a certain period of time causes elongation of the DNA.

Further, the second direction switching valve 207 is operated to switch to a path where the first supply port and the discharge port communicate with each other. Thereby, the sample 120 can move from the medium temperature region 141 to the high temperature region 140 while being pushed inside the channel 112 toward the first communication port 117. When the sample 120 reaches the high temperature region 140, the second direction switching valve 207 is operated to switch to a path where the second supply port and the discharge port communicate with each other. Thereby, the pressure in the space on the second communication port 118 side of the sample 120 becomes the same as the pressure inside the pressurizing chamber 201, and the pressure in the space on the second communication port 118 side becomes equal to the pressure on the first communication port 117 side. Thus, the sample 120 stops moving. Placing the sample in the high temperature region 140 for a certain period of time causes denaturation of the DNA.

By controlling the operation of the first direction switching valve 206 and the second direction switching valve 207 of the liquid feeding system 237 so as to repeat the movement of the sample 120 described above, the sample 120 is allowed to reciprocate inside the channel 112. More specifically, the sample 120 cyclically passes through the respective regions of the temperatures: a high temperature (denaturation); a low temperature (annealing); a medium temperature (elongation); a high temperature (denaturation); a low temperature (annealing); a medium temperature (elongation); and so on. Further, in the case of a reaction processor where temperature regions of two levels are set, the sample 120 cyclically passes through the respective regions of the temperatures: a high temperature (denaturation); a medium-low temperature (annealing and elongation); a high temperature (denaturation); a medium-low temperature (annealing and elongation); and so on. This allows a predetermined number of thermal cycles to be applied to the sample 120 and allows PCR to occur such that predetermined DNA can be selectively amplified.

As described above, in the reaction processor 230 according to the third embodiment, the pressure inside the channel 112 of the reaction processing vessel 110 is always maintained to be higher than the air pressure in the surrounding environment of the reaction processor 230, more preferably 1 atm or higher, during the reaction process. In other words, the sample 120 is constantly pressurized to be higher than the air pressure in the surrounding environment maintained in the pressurizing chamber 201, more preferably 1 atm (1013 hPa) or higher, or pressurized by the pressure in the liquid feeding chamber 200, which is higher than the pressure in the pressurizing chamber 201. Therefore, PCR can be performed while preventing the boiling of a sample and the generation of air bubbles even in a place where the air pressure is low such as a high altitude place or the inside of an airplane.

The reaction processors according to the present invention have been explained above. In the case of a reaction processor unrelated to the reaction processors according to the present invention, that is, in the case of a reaction processor according to an embodiment where a sample in a channel is not pressurized, the sample may easily boil and/or foam when PCR is performed under a low air pressure environment such as a high altitude place or the inside of an airplane. Foamed bubbles are often generated in the middle of the sample, and a plurality of bubbles are often generated. In that case, a phenomenon occurs in which the pressure in the bubbles generated between pieces of the sample and the pressure for liquid feeding and the like start to be balanced such that the liquid feeding cannot be performed smoothly, e.g., a part of the sample stops in the channel.

According to the reaction processors according to the present invention described above, the probability of foaming can be drastically reduced in the first place such that the above problem does not arise and, even under any air pressure environment, the feeding of a sample can be performed in an almost perfect manner, and as a result, amplified samples such as DNA can be obtained through a stable reaction process.

Described above is an explanation of the present invention based on the embodiments. These embodiments are intended to be illustrative only, and it will be obvious to those skilled in the art that various modifications to constituting elements and processes could be developed and that such modifications are also within the scope of the present invention.

What is claimed is:

1. A reaction processor that performs a reaction process of a sample by applying a thermal cycle to the sample, comprising:
    a reaction processing vessel that has a channel in which the sample can move, a first communication port that is provided at one end of the channel, and a second communication port that is provided at the other end of the channel;
    a pressurizing chamber in which, during the reaction process, an internal volume is constant and the internal pressure thereof is maintained at a constant value that is higher than the air pressure in the surrounding environment of the reaction processor;
    a first liquid feeding pump comprising a micro blower with a first output port in communication with the first communication port, the first liquid feeding pump being disposed inside the pressurizing chamber and being operative to suck air in the pressurizing chamber and discharge air into the channel first communication port via the first output port;
    a second liquid feeding pump comprising a micro blower with a second output port in communication with the second communication port, the second liquid feeding pump being disposed inside the pressurizing chamber and being-operative to suck air in the pressurizing chamber and discharge air into the second communication port via the second output port;
    a temperature control system, comprising at least a heat source and a temperature sensor, that forms a plurality of different temperature regions in the channel; and
    a processor-based control unit operative to control operation of said first and second pumps as well as the temperature control system;
    wherein the control unit is operative to maintain pressure inside the channel to be higher than the air pressure in the surrounding environment of the reaction processor by controlling the first liquid feeding pump and the second liquid feeding pump,
    wherein the control unit is operative to maintain pressure inside the channel to be equal to or more than the pressure inside the pressurizing chamber,
    wherein the control unit is operative to control movement of the sample between the plurality of temperature regions by operating either one of the first liquid feeding pump and the second liquid feeding pump, and
    wherein the control unit is operative to stop the sample inside the temperature regions by stopping the first liquid feeding pump and the second liquid feeding pump such that the pressures in the spaces on respective sides of the sample inside the channel are equal to the pressure inside the pressurizing chamber.

2. The reaction processor according to claim 1, wherein the sample includes DNA, a PCR reagent, and a reagent that emits fluorescence, and wherein the reaction process involves PCR.

3. The reaction processor according to claim 1, further comprising a fluorescence detector for detecting fluorescence emitted from the sample inside the channel connecting the temperature regions,
    wherein the first liquid feeding pump and the second liquid feeding pump are controlled in order to move and stop the sample based on a signal from the fluorescence detector.

4. The reaction processor according to claim 3, wherein the progress of DNA amplification is provided in real time by continuously monitoring a fluorescence signal from the fluorescence detector during a reaction process by the thermal cycle.

5. The reaction processor according to claim 1, wherein the plurality of temperature regions are formed by either the following (i) or the following (ii):
    (i) a denaturation region maintained at a temperature that causes thermal denaturation of the sample, an annealing region maintained at a temperature that causes annealing, and an elongation region maintained at a temperature that causes elongation; and
    (ii) a denaturation region maintained at a temperature that causes thermal denaturation of the sample and an annealing and elongation region maintained at a temperature that causes annealing and elongation.

6. The reaction processor according to claim 1, wherein the sample is moved between the plurality of temperature regions by operating either one of the first liquid feeding pump and the second liquid feeding pump while stopping the other such that, in the spaces on respective sides of the sample inside the channel, the pressure in the space communicating with the operating liquid feeding pump becomes higher than the pressure inside the pressurizing chamber and the pressure in the space communicating with the stopped liquid feeding pump becomes equal to the pressure inside the pressurizing chamber.

7. The reaction processor according to claim 1, wherein the temperature control system heat source comprises a plurality of heaters.

8. The reaction processor according to claim 1, wherein the temperature control system further comprises a heat source driver.

9. The reaction processor according to claim 1, further comprising pump drivers coupled to the first and second pumps.

10. The reaction processor according to claim 1, further comprising flow direction switching valves operative under control of the control unit.

11. A reaction processor that performs a reaction process of a sample by applying a thermal cycle to the sample, comprising:
   a reaction processing vessel that has a channel in which the sample can move, a first communication port that is provided at one end of the channel, and a second communication port that is provided at the other end of the channel;
   a pressurizing chamber in which, during the reaction process, an internal volume is constant and the internal pressure thereof is maintained to be constant and higher than the air pressure in the surrounding environment of the reaction processor;
   a first liquid feeding pump comprising a micro blower with a first output port in communication with the first communication port, the first liquid feeding pump being disposed inside the pressurizing chamber and being operative to suck air in the pressurizing chamber and discharge air into the channel first communication port via the first output port;
   a second liquid feeding pump comprising a micro blower with a second output port in communication with the second communication port, the second liquid feeding pump being disposed inside the pressurizing chamber and being-operative to suck air in the pressurizing chamber and discharge air into the second communication port via the second output port;
   a temperature control system, comprising at least a heat source and a temperature sensor, that forms a plurality of different temperature regions in the channel; and
   a processor-based control unit operative to control operation of said first and second pumps as well as the temperature control system;
   wherein the control unit is operative to maintain pressure inside the channel to be higher than the air pressure in the surrounding environment of the reaction processor via the first liquid feeding pump and the second liquid feeding pump,
   wherein the control unit is operative to maintain pressure inside the channel equal to or more than the pressure inside the pressurizing chamber,
   wherein the control unit is operative to move the sample between the plurality of temperature regions by operating either one of the first liquid feeding pump and the second liquid feeding pump,
   wherein the control unit is operative to stop the sample inside the temperature regions by stopping the first liquid feeding pump and the second liquid feeding pump such that the pressures in the spaces on respective sides of the sample inside the channel are equal to the pressure inside the pressurizing chamber, and
   wherein the first liquid feeding pump and the second liquid feeding pump are pumps that allow the pressure on a primary side and the pressure on a secondary side to be equal to each other when stopped.

* * * * *